(12) United States Patent
Lipps et al.

(10) Patent No.: US 7,264,808 B2
(45) Date of Patent: Sep. 4, 2007

(54) SYNTHETIC PEPTIDE FOR NEUROLOGICAL DISORDERS

(76) Inventors: Binie V. Lipps, 4509 Mimosa Dr., Bellaire, TX (US) 77401; Frederick W. Lipps, 4509 Mimosa Dr., Bellaire, TX (US) 77401

( * ) Notice: Subject to any disclaimer, the term of this patent is extended or adjusted under 35 U.S.C. 154(b) by 547 days.

(21) Appl. No.: 10/716,981

(22) Filed: Nov. 19, 2003

(65) Prior Publication Data

US 2004/0077545 A1    Apr. 22, 2004

Related U.S. Application Data

(63) Continuation of application No. 09/613,355, filed on Jul. 11, 2000, now abandoned.

(51) Int. Cl.
| | |
|---|---|
| A61K 38/00 | (2006.01) |
| A61K 39/00 | (2006.01) |
| C07K 4/00 | (2006.01) |
| C07K 7/08 | (2006.01) |
| C07K 14/00 | (2006.01) |

(52) U.S. Cl. .................. 424/175.1; 530/300; 530/324; 530/326

(58) Field of Classification Search .............. None
See application file for complete search history.

(56) References Cited

U.S. PATENT DOCUMENTS 5,814,603 A * 9/1998 Oldenburg et al. ........... 514/12
6,984,486 B1 * 1/2006 Schubert et al. ............. 435/5

FOREIGN PATENT DOCUMENTS

DE          19508672          * 9/1996

OTHER PUBLICATIONS

Inoue et al. FEBS Lett. 1991; 279: 38-40.*
Haller, MF et al "Nerve Growth Factor Delivery Systems" Journal of Controlled Release vol. 53, 1-6 (1998).
Dicou, Eleni et al "Two Peptides Derived from the nerve Growth Factor Precursor are Biologically Active" J of Cell Biol, vol. 136, No. 2, 389-390 (Jan. 27, 1997).
Beglova et al : "Solution structure . . . of a bioactive peptide . . . " J of Biol. Chem., vol. 273, No. 37., Sep. 11, 1998 pp. 23652-23658.
Longo et al: "Synthetic NGF Peptide . . . " J of Neurosci Res, Wiley Liss, vol. 48, Apr. 1, 1997, pp. 1-17.
Estenne-Bouhtou et al: "Design, synthesis, . . . of NGF Mimetics" Int. J of Peptide and Protein Res., Munksgaard, Copenhagen, DK vol. 48, No. 4, Oct. 1, 1996, pp. 337-346.

* cited by examiner

*Primary Examiner*—Elizabeth Kemmerer
*Assistant Examiner*—Christina Borgeest
(74) *Attorney, Agent, or Firm*—John R Casperson

(57)          ABSTRACT

The purified nerve growth factor consisting of 116 amino acids from the venom of Naja kaouthia snake was fragmented by trypsin digestion. The fragments were isolated individually by high pressure liquid chromatography (HPLC). Thus separated fragments were tested for the biological activity of neurite growth on rat adrenal pheochromocytoma (PC12) cells. The fragment which showed the most activity was named ADESH. Subsequently, ADESH was sequenced. Synthetic ADESH was constructed using ten amino acids N L G E H P V C D S (SEQ. ID. NO: 3) of the fragment from its N-terminal is designated as AD-10. Different versions of synthetic ADESH such as AD-15 and AD-5 consisting of 15 and 5 amino acids respectively were constructed; having the sequence: N L G E H P V C D S T D T W V (SEQ. ID. NO: 2) for AD-15 and N L G E H (SEQ. ID. NO: 4) for AD-5. The synthetic AD-15 and AD-5 mimic the biological activity of the natural NGF.

12 Claims, No Drawings

SEQUENCE LISTING

```
<160> NUMBER OF SEQ ID NOS: 4

<210> SEQ ID NO 1
<211> LENGTH: 116
<212> TYPE: PRT
<213> ORGANISM: Naja naja

<400> SEQUENCE: 1

Glu Asp His Pro Val His Asn Leu Gly Glu His Pro Val Cys Asx Ser
1               5                   10                  15

Thr Asx Thr Trp Val Gly Val Lys Thr Thr Ala Thr Asn Ile Lys Gly
                20                  25                  30

Ala Ser Val Ser Val Met Glu Asn Val Asn Leu Asp Asn Lys Val Tyr
            35                  40                  45

Lys Gln Tyr Phe Phe Glu Thr Lys Cys Arg Asx Ser Asx Pro Pro Glx
    50                  55                  60

Pro Gly Cys Lys Gly Ile Asx Thr Glx His Trp Asx Ser Tyr Cys Thr
65                  70                  75                  80

Thr Ser Asn Ser Phe Ile Lys Ala Leu Thr Met Asx Glx Gly Gln Ser
                85                  90                  95

Ala Trp Arg Phe Ile Arg Ile Glx Thr Ala Cys Val Cys Val Ile Thr
            100                 105                 110

Lys Lys Gly Asn
        115

<210> SEQ ID NO 2
<211> LENGTH: 15
<212> TYPE: PRT
<213> ORGANISM: ARTIFICIAL
<220> FEATURE:
<223> OTHER INFORMATION: SYNTHESIZED.  SIMILAR TO FRAGMENT 7-21 OF SEQ
      ID NO 1 ABOVE.

<400> SEQUENCE: 2

Asn Leu Gly Glu His Pro Val Cys Asp Ser Thr Asp Thr Trp Val
1               5                   10                  15
```

```
<210> SEQ ID NO 3
<211> LENGTH: 10
<212> TYPE: PRT
<213> ORGANISM: ARTIFICIAL
<220> FEATURE:
<223> OTHER INFORMATION: SYNTHESIZED.  SIMILAR TO FRAGMENT 7-16 OF SEQ.
      ID. NO. 1.

<400> SEQUENCE: 3

Asn Leu Gly Glu His Pro Val Cys Asp Ser
1               5                   10

<210> SEQ ID NO 4
<211> LENGTH: 5
<212> TYPE: PRT
<213> ORGANISM: ARTIFICIAL
<220> FEATURE:
<223> OTHER INFORMATION: SYNTHESIZED.  CORRESPONDS TO FRAGMENT 7-11 OF
      SEQ. ID. NO. 1.

<400> SEQUENCE: 4

Asn Leu Gly Glu His
1               5
```

SYNTHETIC PEPTIDE FOR NEUROLOGICAL DISORDERS

CROSS-REFERENCES TO RELATED APPLICATIONS

This application is a continuation of application Ser. No. 09/613,355 filed Jul. 11, 2000, now abandoned.

BACKGROUND OF THE INVENTION

1. Field of the Invention

The invention relates to a synthetic peptide which mimics the biological properties of nerve growth factor (NGF) and is useful for treating neurological disorders.

2. Background of the Invention

Nerve growth factor (NGF) was discovered more than forty years ago by Levi-Montalcini et al. in malignant tissues. Subsequently Cohen isolated NGF from snake venom and then from sub maxillary gland of mouse, a homolog to the snake venom gland. Since the discovery it was contemplated that NGF will be clinically useful to treat neurological disorders, like Alzheimer's (AD), Parkinson's (PD) and other neurological diseases. Over the years, several neurotrophic factors such as NT-3, bFGF, platelet derived growth factor, etc. were discovered. These factors regulate nerve cell growth and survival.

Research in animals has demonstrated that neurotrophic factors delivered to central nervous system can prevent or reverse neurodegeneration. Generally, neurotrophic factors cannot cross the blood-brain barrier due to their size and therefore, will not reach the brain when administered either orally or through injection. As a result, researchers have administered these proteins directly into the brain to determine their effectiveness in combating neurodegenerative diseases. In animals, various neurotrophic factors administered through a hole drilled into the scull have been successful in restoring memory and stimulating nerve regeneration. In humans, nerve growth factor administered in similar way has improved memory in Alzheimer's disease patients.

A more convenient delivery system is required, to produce the beneficial effects that have been established for neurotrophic factors. The selective breakdown of the blood-brain barrier has not proven to be effective as yet. The most practical approach is to mimic the effects of neurotrophic factors by administration of an orally active compound that passes the blood-brain barrier and produces the effects of neurotrophic factors in the brain or turns on the genes to produce neurotrophic factors at the site where they are needed in the brain.

AIT-082 is the first compound that has entered human clinical trials, which has been demonstrated to activate multiple genes in animals to produce three different neurotrophic factors (NGF, NT-3 and bFGF) in the specific areas of the brain associated with memory loss. In addition, AIT-082 has the advantage of being rapidly absorbed and active after oral administration. However, its efficacy remains to be determined.

Appel proposed that selective neuronal degeneration may be caused by failure of target tissues to supply the necessary neurotrophic factor. A specific link between NGF and AD was first suggested by Hefti. It has been reported that NGF level rises in pathological situation such as hypoxic injury in adult rats. Data are already emerging to suggest an age-related reduction in both NGF and its receptor in rat brain.

Naturally occurring bioactive peptides have been proposed for neurological disorders. Appel and Tomozawa 1991 isolated, extracted and purified three different neurotrophic factors from caudate putmen tissue of normal mammal, to treat amyotrophic lateral sclerosis (ALS), PD and AD. Heinrich produced recombinant human (h-NGF) made in Chinese hamster ovary cells. (CHO). Lewis et al. 1992 proposed the use of insulin like growth factor for treating disorders enhancing the survival of non-mitotic cells.

Despite the previous failures to obtain NGF in animal sera, at Ophidia Products we have successfully isolated NGF from human and other animal sera, showing neurotrophic activity when tested on PC12 cells. In addition, we have isolated NGF from human saliva and urine. Furthermore, we have isolated NGF from the established cultures of eukaryotic cells; Chang cells (human liver), Vero (monkey kidney), pheochromocytoma PC12 (rat adrenal gland), neuroblastoma (human brain) and mouse myeloma (SP/2) cells.

According to Wells, 1996 the commonly held view that small synthetic peptides cannot mimic effects of large polypeptide ligands is by now considerably out of date. Several investigators have made synthetic NGF peptide derivatives which prevent neuronal death and show neurite outgrowth, the characteristic of the neurotrophic factor on PC12 cells. Longo et al. (1997) made cyclized peptides corresponding to beta loop region of NGF and found the highest activity corresponding a loop region 29-35 which is capable to interact with p75 receptor. According to them, to this date, no small molecule NGF agonist or partial agonists agents known to promote neurotrophic effects by acting via NGF receptors have been described.

A small molecule which behaves like NGF would be very desirable for treating neurological disorders, since it would overcome the blood-brain barrier. It would be capable of reaching the brain by most any route, for example, intramuscular, intravenous, buccal cavity or nasal insufflation could be used. It may avoid triggering antibody production.

A small molecule which behaves like NGF and can be synthetically produced would be even more desirable, since its production would be straightforward and inexpensive.

OBJECTS OF THE INVENTION

The object of the invention is to provide a peptide consisting of in the range of 5 to 25 amino acids which mimics the activity of NGF. Such a peptide can be synthetically made in abundance to provide therapeutics for neurological disorders. Such a peptide would have a low molecular weight to enable it to reach the brain when administered by most any route.

SUMMARY OF THE INVENTION

The invention relates to a synthetic peptide consisting of at least the first five amino acids from the N-terminal of the sequence N L G E H P V C D S T D T W V (SEQ. ID NO: 2). The synthetic peptide mimics the biological properties of nerve growth factor (NGF) consisting of 116 amino acids.

The peptide of the invention can be administered to a patient having a neurological disorder by various routes, including injection and orally. The peptide of the invention can reach the brain as a small molecule without blood-brain barrier problem, since it is small enough to cross the blood-brain barrier.

Antibodies made against the peptide of the invention have a higher binding affinity for NGF of human origin (termed H-NGF) than antibodies which were made against the 116 amino acid NGF derived from venom (V-NGF, the antibody being Anti-V-NGF). This fact evidences that the composition of the inventive peptide is a conserved domain of the activity of human NGF. Therefore, the inventive peptide is immunologically closer to H-NGF than V-NGF.

Antibodies made against the inventive peptide can be used assay NGF levels in human bodily fluids such as saliva and urine for diagnostic purposes without the necessity of extracting blood.

DETAILED DESCRIPTION OF THE INVENTION

The inventive peptides can be generally described as compositions of matter consisting of at least the first five amino acids from the N-terminal of the sequence N L G E H P V C D S T D T W V (SEQ. ID NO: 2) and no more than 25 amino acids total. Usually, the inventive peptides will contain no more than 20 amino acids, and preferably no more than 15 amino acids. I have named the inventive peptides ADESH.

ADESH which contains only a portion of the amino acid sequence is preferred. ADESH which contains only the first five amino acids of the sequence is termed AD-5. ADESH which contains only the first 10 amino acids of the sequence is termed AD-10, and is the preferred species. ADESH which contains only the first fifteen amino acids of the sequence is termed AD-15. AD-5, AD-10 and AD-15 have been tested on PC12 cells and found to be biologically active in producing neurite outgrowth.

ADESH constitutes a nerve growth factor preferably having in the range of 5 to 20 amino acids, and capable of crossing the blood-brain barrier. It can be effectively utilized by patients having a need of nerve growth factor by delivering it to the bloodstream. Examples of patients for whom ADESH treatment should be beneficial include victims of Alzheimer's disease (AD) and Parkinson's disease (PD). Suitable routes of administration include nasal insufflation, buccal administration, oral ingestion, and intramuscular injection. ADESH can also be injected directly into the blood stream.

ADESH mimics the biological properties of NGF derived from cobra venom. Venom-derived NGF is termed V-NGF. The property of V-NGF most interest which is mimicked by ADESH is the stimulation of neurite outgrowths.

The amino acid sequence of V-NGF derived from one species of cobra (Naja naja) venom is:
NH2-Glu-Asp-His-Pro-Val-His-Asn-Leu-Gly-Glu-His-Pro-Val-Cys-Asx-Ser-Thr-Ash-Thr-Trp$_{20}$-Val-Gly-Val-Lys-Thr-Thr-Ala-Thr-Asn-Ile-Lys-Gly-Ala-Ser-Val-Ser-Val-Met-Glu-Asn$_{40}$-Val-Asn-Lys-Val-Tyr-Lys-Gln-Tyr-Phe-Phe-Glu -Thr-Lys-Cys-Arg-Asx-Ser$_{60}$-Asx-Pro-Pro-Glx-Pro-Gly-Cys-Lys-Gly-Ile-Asx-Thr-Glx-His-Trp-Asx-Ser-Tyr-Cys-Thr$_{80}$-Thr-Ser-Asn-Ser-Phe-Ile-Lys-Ala-Leu-Thr-Met-Asx-Glx-Gly-Gln-Ser-Ala-Trp-Arg-Phe$_{100}$-Ile-Arg-Ile-Gix-Thr-Ala-Cys-Val-Cys-Val-Ile-Thr-Lys-Lys-Gly-Asn-COOH
(SEQ. ID. NO: 1)

In vivo, ADESH causes the immunized animal to produce an antibody which has a binding 15 affinity to NGFs from human bodily fluids and human-origin eukaryotic cells which is higher than a binding affinity exhibited by an antibody produced in immunological response to V-NGF. Synthetic ADESH is equally active as the fragment of the native NGF. Antibodies made against ADESH (Anti-ADESH) react with V-NGF having 116 amino acids. However, antibodies made against V-NGF (Anti-V-NGF) react poorly with ADESH. This illustrates that the ten amino acids of ADESH are essentially important for the biological activity of neurite growth Therefore, synthetic ADESH consisting of ten amino acids, especially, is a candidate for the treatment of neurological disorders instead of the entire NGF molecule.

In the past, there were failures to detect and/or quantify Human NGF (H-NGF) in human serum. Our research shows that H-NGF will can be quantified in vitro by contacting sample fluids with an Anti-ADESH. The contacting is preferably carried out so as to cause the antibody to react immunologically with the NGF contained in the sample fluid. The test has been shown effective in quantifying H-NGF contained in samples of blood serum, saliva and urine.

EXPERIMENTAL AND RESULTS

Purification of NGF from Snake venom

Homogenous preparation of NGF was obtained by fractionating snake venom from Naja kaouthia by HPLC using ion exchange column and gradient Trizma-HCl buffer pH 7.4.

Trypsin Digestion of Natural NGF

Purified homogenous preparation of NGF was treated with trypsin dissolved in 0.1 M ammonium bicarbonate buffer pH 8.0. The NGF and the trypsin were mixed in 40:1 ratio, precisely 5 mg of NGF to 0.25 mg of trypsin. The mixture was incubated at 37° C. to cause fragmentation at arginine and lysine sites. After 18 hours of incubation the reaction was stopped by cooling the mixture at 4° C.

Separation of Fragments from Trypsin Digest

The trypsin digested fragments were separated on HPLC. The separation was done in two runs by loading half the mixture each time. Trypsin digested NGF resolved into ten different fragments. The fragments were collected individually and dialyzed against water using 500 daltons molecular weight cutoff tubing (Spectrum USA). The protein concentration of each fragment was measured by using Bio-Rad (USA) protein kit and the concentration of each fragment was adjusted to 100 µg/ml with 0.05 M phosphate buffered saline (PBS).

Biological Activity of Fragments PC12 Cells

The trypsin digested fragments in various concentrations were tested for neurite out growth on PC12 cells. Tissue culture plate having 24 wells were seeded with $10^5$ PC12 cells in serum free Dulbeco Modified Eagle's medium (DMEM). The results were read after 72 hours for neurite outgrowth. The fraction showing the most neurite outgrowth at the lowest concentration was sequenced for its amino acids composition. Sequencing was contracted out to the Protein Core Laboratory of Baylor College of Medicine, Houston, Tex. The sequence for the fraction from the N-terminal was found to be: N L G E H P V C D S T D T W V (SEQ. ID. NO: 2)

Synthesis of ADESH

Synthetic ADESH (AD-10) was constructed using the above amino acids sequence from N-terminal for ten amino acids N L G E H P V C D S (SEQ. ID. NO: 3). Two more versions of synthetic ADESH, termed AD-15 and AD-5, consisting of 15 and 5 amino acids respectively, were constructed; The peptides had the sequence: N L G E H P V C D S T D T W V (SEQ. ID. NO: 2) for AD-15 and N L G E H (SEQ. ID. NO: 4) for AD-5.

Production of Polyclonal Antibodies to ADESH in Mice

There is a perception that small synthetic peptides do not generate antibodies on injection into animals. However, synthetic peptide can generate antibodies if it is tagged with a complete protein, before injecting to the animal. Landsteiner coined the term hapten for a low molecular weight, chemically defined compound which could induce antibody formation only when coupled to larger carrier protein molecule before injecting. Thereby, the injected animal makes antibodies to both the hapten and the carrier protein.

Synthetic chemically defined ADESH comprising fifteen, ten or five amino acids can be considered as haptens and therefore, theoretically should not induce antibodies if injected without a carrier protein. However, for our other projects, we have succeeded generating antibodies in mice for a synthetic peptide consisting of five amino acids.

Adult Balb/C mice were used for immunization. The mice were used in compliance with the US Public Health Service Policy on humane care and use of animals. First injection consisted of the mixture 100 μg of each version of ADESH in 0.1 ml mixed with equal volume of Freund's complete adjuvant/mouse. The subsequent injections consisted of the mixture 100 μg of ADESH and equal volume of incomplete Freund's adjuvant/mouse. The mice were injected intramuscularly (IM) six times two weeks apart. At the end of the immunization the mice were bled through the ophthalmic veins and serum was separated.

Enzyme-Linked Immunosorbent Assay (ELISA): The binding affinity of Anti-ADESH made against ADESH consisting of ten amino acids (AD-10), to various specimens known to contain NGF, such as venoms, body fluids, saliva, serum, urine etc. was studied by ELISA. The ELISA binding of Anti-AD-10 was compared to Anti-NGF made against cobra venom. ELISA tests were performed in 96 well microtiter plate. The wells of the plate were coated with one concentration of antigen, diluted in PBS each well receiving 100 μL. The plate was incubated at room temperature (RT) for 16 to 18 hours after which it was three times (3×) with PBS. The wells of the plate were blocked with 0.25 ml/well of 3% Teleostean gelatin from cold water fish (Sigma) for ½ hour at RT. Anti-AD-10 and Anti-NGFs were diluted threefold in gelatin were added to the appropriate wells of ELISA plate, including positive and negative controls. The plate was incubated at 37° C. for 1 to 1.5 hours. After washing 3X times horseradish peroxidase conjugated with IgG made in goat (Sigma) was added and incubated for 1 hour. Finally, the plate was washed and reacted with O-Phenylenediamine Dihydrochloride (OPD) for color development. The test was after ½ hour for ELISA titers.

Isolation of NGF from Body Fluids: Concentrated body fluids such as saliva, serum and urine were fractionated on HPLC by our proprietary procedure. Each type fluid resolved into several fractions. The fractions were dialyzed and tested for neurotrophic activity of PC12 cells. The identified fraction of NGF was further repurified to obtain homogenous NGF. NGFs were also isolated from cobra snake serum and from honey bee venom.

Isolation of NGF from Established Eukaryotic Cells: The cells grown in tissue culture medium DMEM was concentrated before fractionating on HPLC, for isolation of NGF. Each type of cell medium resolved into several fractions. The fractions were dialyzed and tested for neurotrophic activity of PC12 cells. The identified fraction of NGF was further repurified to obtain homogenous NGF. The cell cultures used were Chang liver, Vero, PC12, Neuroblastoma and SP/2 cells and the procedure for isolation followed was similar as described above.

RESULTS

TABLE I

Biological Properties of Different Versions of ADESH compared to Venom NGF

| Specimen | Neurites on PC12 | Toxicity to PC12 | Source | #amino acids | Mol. wt. |
|---|---|---|---|---|---|
| V-NGF | 5 ng | 5 μg | Venom | 16 | 13,500 |
| AD-15 | 1 μg | >100 μg | Synthetic | 15 | 1,921 |
| AD-10 | 1 μg | >100 μg | Synthetic | 10 | 1230 |
| AD-5 | 2 μg | >100 μg | Synthetic | 5 | 640 |

The results of Table 1 show that
(1) the venom derived NGF is toxic at the concentration of 5 μg/ml while AD-15, AD-10 and AD-5 are not toxic up to 100 μg/ml on PC12 cells.
(2) Venom derived NGF produces neurite outgrowth at 5 ng/ml on PC12 while each AD-15, AD-10 and AD-5 requires 1000 ng/ml, 200 times the concentration of venom NGF.
(3) AD-5, AD-10 and AD-15 mimic the property of whole natural NGF in producing neurites on PC12 cells. These properties indicate that AD-5, AD-10 and AD-15 is an integral part of the whole molecule NGF.

TABLE II

Immunological Properties of AD-15, AD-10 and AD-5: ELISA titer for Binding Affinity to Anti-AD-10, Anti-V-NGF and Anti-H-NGF

| Specimen | Anti-AD-10 | Anti-H-NGF | Anti-H-NGF |
|---|---|---|---|
| V-NGF | 900 | 24300 | 1800 |
| AD-15 | 1800 | 600 | 900 |
| AD-10 | 2700 | 450 | 900 |
| AD-5 | 600 | 300 | 600 |
| H-NGF serum | 2700 | 2700 | 24300 |
| H-NGF saliva | 2700 | 1800 | 8100 |
| H-NGF urine | 2700 | 1800 | 8100 |

Results of Table II show that
(1) Anti-AD-10 reacts with NGFs derived from venom, human body fluids; serum, saliva and urine, AD-15 and AD-5.
(2) Binding affinity of Anti-AD-10 is greater to the human source NGFs than venom NGF.
(3) Anti-V-NGF reacts poorly to AD-15, AD-10 and AD-5 in comparison to Anti-H-NGF.

The binding property of Anti-AD-10 to the natural source NGFs illustrates that AD-10 is an integral part and closer to human NGF.

TABLE III

ELISA Titers of Anti-AD-10 and Anti-V-NGF to Venoms

| Specimen | Anti-AD-10 | Anti-V-NGF |
|---|---|---|
| C. atrox | 300 | 900 |
| N. n. kaouthia | 600 | 5400 |

TABLE III-continued

ELISA Titers of
Anti-AD-10 and Anti-V-NGF to Venoms

| Specimen | Anti-AD-10 | Anti-V-NGF |
| --- | --- | --- |
| D. russelli | 450 | 1800 |
| O. Scutellatus | 450 | 1800 |
| Honey Bee | 300 | 2700 |
| Scorpion | 300 | 2700 |

It is known that snake venoms contain NGF and recently Lipps (1999) has reported that honey bee and scorpion venoms also contain NGF. Results of Table III demonstrate that
(1) Anti-ADESH show binding affinity to venoms similarly to Anti-V-NGF.
(2) This property illustrates that synthetic ADESH consisting of ten amino acids is an integral part of V-NGF which has greater than 60% homology to human NGF.

TABLE IV

ELISA Binding Affinity of Anti-ADESH, Anti-Venom NGF and Anti-Human NGF to NGFs from Various Sources.

| Cell Type | Origin | Anti-ADESH | Anti-H-NGF | Anti-V-NGF |
| --- | --- | --- | --- | --- |
| Chang | human | 8100 | 16200 | 2700 |
| NB | human | 8100 | 16200 | 2700 |
| PC12 | rat | 200 | 300 | 2700 |
| Vero | monkey | 900 | 300 | 2700 |
| SP2 | mouse | 900 | 1800 | 600 |

Results of Table IV illustrate that:
(1) Anti-ADESH has highest binding affinity to NGFs derived human source (Chang, NB cells), lesser to monkey and mouse (Vero, SP/2), and least to rat (PC12) cell derived NGF.
(2) The binding affinity of Anti-ADESH is similar to Anti-H-NGF. This shows that a synthetic peptide ADESH is closer to human NGF is pleasing as ADESH is proposed to treat humans.

What is claimed is:

1. A composition of matter comprising a peptide and a carrier, said peptide consisting of
   a sequence of no more 25 amino acid residues linked by peptide bonds, said sequence of amino acid residues including SEQ ID NO:4.

2. A composition of matter as in claim 1 wherein the peptide consists of a sequence of no more than 15 amino acid residues linked by peptide bonds.

3. A composition of matter as in claim 2 wherein the sequence of amino acid residues includes SEQ. ID. NO.: 3.

4. A composition of matter as in claim 1 wherein the peptide produces an antibody in an animal immunized with the peptide which has a binding affinity to NGFs from human blood serum, saliva and urine which is higher than a binding affinity exhibited by an antibody produced in an animal immunized with SEQ ID NO: 1.

5. A method of using a composition of matter as m claim 1 comprising forming antibodies against the peptide, and
   contacting, in vitro, a human nerve growth factor with the antibodies so as to cause the antibodies to react immunologically with the human nerve growth factor.

6. A process comprising contacting, in vitro, a human nerve growth factor with an antibody made in an animal against a peptide as recited in claim 1.

7. A process as in claim 6 wherein the contacting is carried out so as to cause the antibody to react immunologically with the human nerve growth factor.

8. A peptide comprising SEQ ID NO: 4 beginning at the N-terminal and having a sequence length of no more than 25 amino acid residues.

9. A peptide as in claim 8 having a sequence length of no more than 15 amino acid residues.

10. A peptide as in claim 9 comprising SEQ II) NO: 3.

11. A peptide selected from the group consisting of SEQ ID NO: 2 and a fragment of SEQ ID NO: 2 comprising SEQ ID NO: 4.

12. A peptide as in claim 11 which consists of SEQ ID NO: 3.

* * * * *